United States Patent
Barry et al.

(10) Patent No.: US 12,133,670 B2
(45) Date of Patent: *Nov. 5, 2024

(54) METHOD FOR TREATING EMPHYSEMA WITH CONDENSABLE THERMAL VAPOR

(71) Applicant: Uptake Medical Technology Inc., Seattle, WA (US)

(72) Inventors: Robert Barry, Kirkland, WA (US); Erik Henne, Seattle, WA (US)

(73) Assignee: Uptake Medical Technology Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/892,378

(22) Filed: Aug. 22, 2022

(65) Prior Publication Data
US 2022/0395309 A1 Dec. 15, 2022

Related U.S. Application Data (63) Continuation of application No. 16/143,321, filed on Sep. 26, 2018, now Pat. No. 11,419,658.

(Continued)

(51) Int. Cl.
*A61B 18/04* (2006.01)
*A61B 18/00* (2006.01)
(Continued)

(52) U.S. Cl.
CPC .... *A61B 18/04* (2013.01); *A61B 2018/00541* (2013.01); *A61B 2018/00577* (2013.01); *A61B 2018/00982* (2013.01); *A61B 2018/048* (2013.01); *A61B 18/1492* (2013.01); *A61M 31/00* (2013.01)

(58) Field of Classification Search
CPC ............... A61B 2018/00541; A61B 18/04
See application file for complete search history.

(56) References Cited

U.S. PATENT DOCUMENTS

| | | | |
|---|---|---|---|
| 8,021,320 B2 * | 9/2011 | Tanaka | A61M 16/202 604/47 |
| 2009/0192505 A1 * | 7/2009 | Askew | A61M 16/0463 424/9.4 |

(Continued)

OTHER PUBLICATIONS

Valipour, A., Herth, F. J., Eberhardt, R., Shah, P. L., Gupta, A., Barry, R., . . . Snell, G. (2014). Design of the randomized, controlled sequential staged treatment of emphysema with upper lobe predominance (step-up) study. BMC Pulmonary Medicine, 14(1). doi: 10.1186/1471-2466-14-190. (Year: 2014).*

(Continued)

*Primary Examiner* — Joseph A Stoklosa
*Assistant Examiner* — Annie L Shoulders
(74) *Attorney, Agent, or Firm* — Batt IP A Law Corporation; Richard Batt (57) ABSTRACT

A method for treating emphysema with a condensable vapor includes creating a plurality of collateral channels through the airway walls, and delivering the condensable vapor to the airways. The condensable vapor flows to the diseased parenchymal tissue through the airways and the collateral channels. Condensable vapor to contact the tissue heats the tissue, reducing it in volume. Apparatuses are described to create the openings and ablate the lung tissue.

18 Claims, 9 Drawing Sheets

Related U.S. Application Data

(60) Provisional application No. 62/582,220, filed on Nov. 6, 2017.

(51) Int. Cl.
*A61M 31/00* (2006.01)
*A61B 18/14* (2006.01)

(56) References Cited

U.S. PATENT DOCUMENTS

| | | | | |
|---|---|---|---|---|
| 2012/0289776 A1* | 11/2012 | Keast | ............... | A61B 17/0293 600/114 |
| 2015/0094607 A1* | 4/2015 | Barry | ............... | A61B 34/10 600/538 |
| 2015/0272718 A1* | 10/2015 | Clark | ............... | A61F 2/04 623/23.65 |
| 2016/0151103 A1* | 6/2016 | Henne | ............... | A61B 18/04 604/26 |

OTHER PUBLICATIONS

Charalampidis C, Youroukou A, Lazaridis G, etc., Pleura space anatomy. J Thorac Dis. Feb. 2015;7(Suppl 1):S27-32. doi: 10.3978/j.issn.2072-1439.2015.01.48. PMID: 25774304; PMCID: PMC4332049. (Year: 2015).*

* cited by examiner

METHOD FOR TREATING EMPHYSEMA WITH CONDENSABLE THERMAL VAPOR

CROSS-REFERENCE TO RELATED APPLICATIONS

This application is a continuation application of U.S. patent application Ser. No. 16/143,321, filed Sep. 26, 2018, entitled "METHOD FOR TREATING EMPHYSEMA WITH CONDENSABLE THERMAL VAPOR" and claims benefit and priority to provisional patent application No. 62/582,220, filed Nov. 6, 2017, and entitled "METHOD FOR TREATING EMPHYSEMA WITH CONDENSABLE THERMAL VAPOR."

BACKGROUND OF THE INVENTION

This invention relates to medical devices, systems and methods, and in particular to intrabronchial catheters, systems and methods for delivering a condensable vapor to diseased tissue in a patient's lungs.

Heating therapies are increasingly used in various medical disciplines including pulmonology, cardiology, dermatology, orthopedics, oncology as well as a number of other medical specialties. In general, the manifold clinical effect of super physiological tissue temperatures results from underlying molecular and cellular responses, including expression of heat-shock proteins, cell death, protein denaturation, tissue coagulation and ablation. Associated with these heat-induced cellular alternations and responses are dramatic changes in tissue structure, function and properties that can be exploited for a desired therapeutic outcome such as tissue injury, shrinkage, modification, destruction and/or removal.

Heating techniques in the lung pose several technical challenges because lung tissue is more aerated than most tissues and also due to its vascularization. Accordingly, these new heating methods, devices and systems for rapid, controllable, effective and efficient heating of lung tissue are needed. The present invention is directed at meeting these as well as other needs.

SUMMARY OF THE INVENTION

Methods for treating emphysema include reducing the lung volume of the diseased tissue, and fixing the diseased tissue while it is in the reduced state.

In embodiments, at least one collateral channel or opening is created through the airway walls of a hyperinflated lung segment. Condensable vapor is delivered into the lung segment via the airway. The condensable vapor naturally traverses distally through the airways into the parenchyma. Additionally, some of the vapor traverses through the newly created openings into the parenchyma providing a second or ancillary modality for diseased tissue ablation and lung volume reduction (LVR).

Without intending to be bound by theory, acutely and significantly reducing the hyperinflated segments by creating openings through the airway walls and then delivering the condensable vapor is beneficial because the novel method remodels the treated lung by fixing the lung segments in the reduced state through collagen strands that develop as a result of diseased tissue replacement. Substantial volume reduction remains permanent despite the openings potentially closing over time.

Additionally, embodiments of the subject invention have several advantages over use of implants to carry out LVR. Particularly, because embodiments of the subject invention do not require implants, the number of complications associated with LVR implants is reduced. Additionally, the surgically created openings serve to drain the lung segment during the above mentioned remodeling period and therefore reduce the risk of pneumonia.

The quantity and the location of the openings to be created may vary widely. In embodiments, at least one opening is created in the airways distal to where condensable vapor will be delivered to the airway. This can have the advantage of maintaining the openings patent longer compared to other treatment modalities such as, for example, applying direct heat to the opening. Applying direct heat (e.g., resistive or RF-based heat) to the opening can undesirably increase cell proliferation leading to hole closure prior to the remodeling (perhaps a 4 to 6-week process).

In embodiments, openings are created in each of the segmental airways in order to reduce the overall hyperinflation of the lobe, and then condensable vapor is applied to the most diseased segment(s). Determination of the most diseased segments may be performed by, e.g., CT scan, and other diagnostic testing.

Condensable vapor can be applied proximally or distally to the surgically created openings. In embodiments, the condensable vapor is delivered from a vapor delivery catheter advanced into the airway to a desired location. In some embodiments, the vapor delivery catheter is advanced through the surgically created openings and the condensable vapor is delivered beyond the airway walls and directly into the target tissue.

In other embodiments, vapor is delivered to the openings only and not within the airways. In one embodiment, vapor is delivered to the openings-only via a balloon catheter. The balloon catheter includes two inflatable members separated axially. The balloon catheter is advanced through the opening until the two inflatable members contain the opening. Vapor can be delivered from an egress aperture in the shaft of the catheter and into the space defined by the two balloons. An advantage of delivering vapor and treating the opening-only is that less mucociliary transport disruption occurs compared to delivering vapor and treating all of the airways. Additionally, the lack of disruption may reduce the likelihood of pneumonia through better liquid clearance of the treated segment.

In other embodiments, a closure (e.g., an occlusion) is created along an airway in a hyperinflated segment by applying a concentration of vapor at the segmental airway using a dual balloon catheter.

The method of forming a closure or occlusion along the airway can be performed in addition to any of the methods described herein. Indeed, all steps described herein may be combined in any logical manner and sequence except where such steps would exclude one another.

In one embodiment, for example, the method of forming an occlusion is followed by the step of creating one or more openings. The openings may be created 4 to 6 weeks after the occlusion ablation. In other embodiments, the openings are created more than 6 weeks from the occlusion ablation. Once the airway has been occluded (e.g., after 4 to 6 weeks from the occlusion procedure), openings are made in the airways of the diseased segment to relieve the hyperinflated volume of the diseased segment. Optionally, vapor is applied through the surgically created openings serving to remodel, seal and fix the lung segment in the reduced state.

Still other descriptions, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 1:
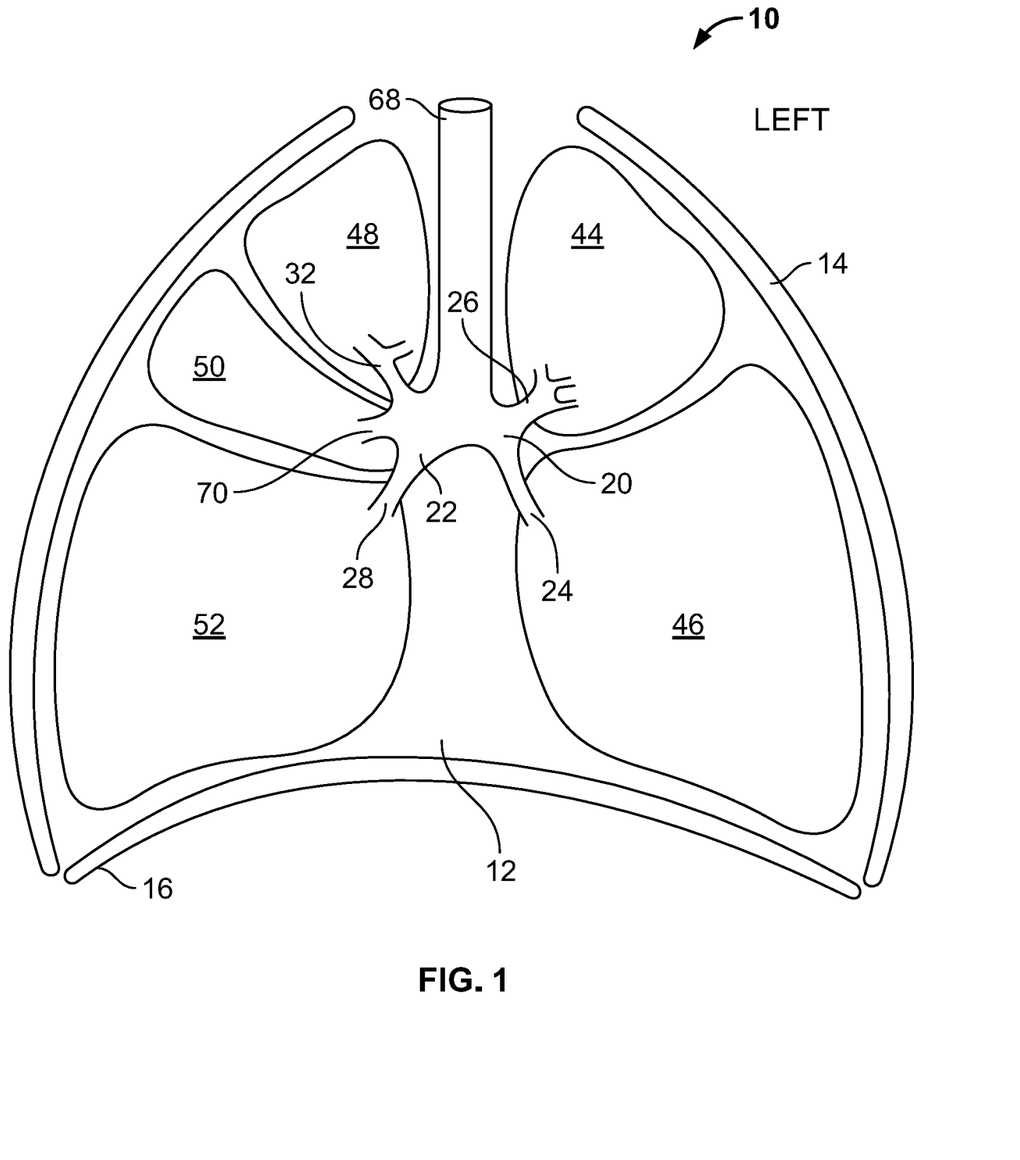
FIG. 1 illustrates a human respiratory system.

FIG. 1 illustrates a human respiratory system 10. The respiratory system 10 resides within the thorax 12 that occupies a space defined by the chest wall 14 and the diaphragm 16. The human respiratory system 10 includes left lung lobes 44 and 46 and right lung lobes 48, 50, and 52.

The respiratory system 10 further includes trachea 18; left and right main stem bronchus 20 and 22 (primary, or first generation) and lobar bronchial branches 24, 26, 28, 30, and 32 (second generation). Segmental and sub-segmental branches further bifurcate off the lobar bronchial branches (third and fourth generation). Each bronchial branch and sub-branch communicates with a different portion of a lung lobe, either the entire lung lobe or a portion thereof. As used herein, the term "air passageway" or "airway" means a bronchial branch of any generation, including the bronchioles and terminal bronchioles.

Figure 2:
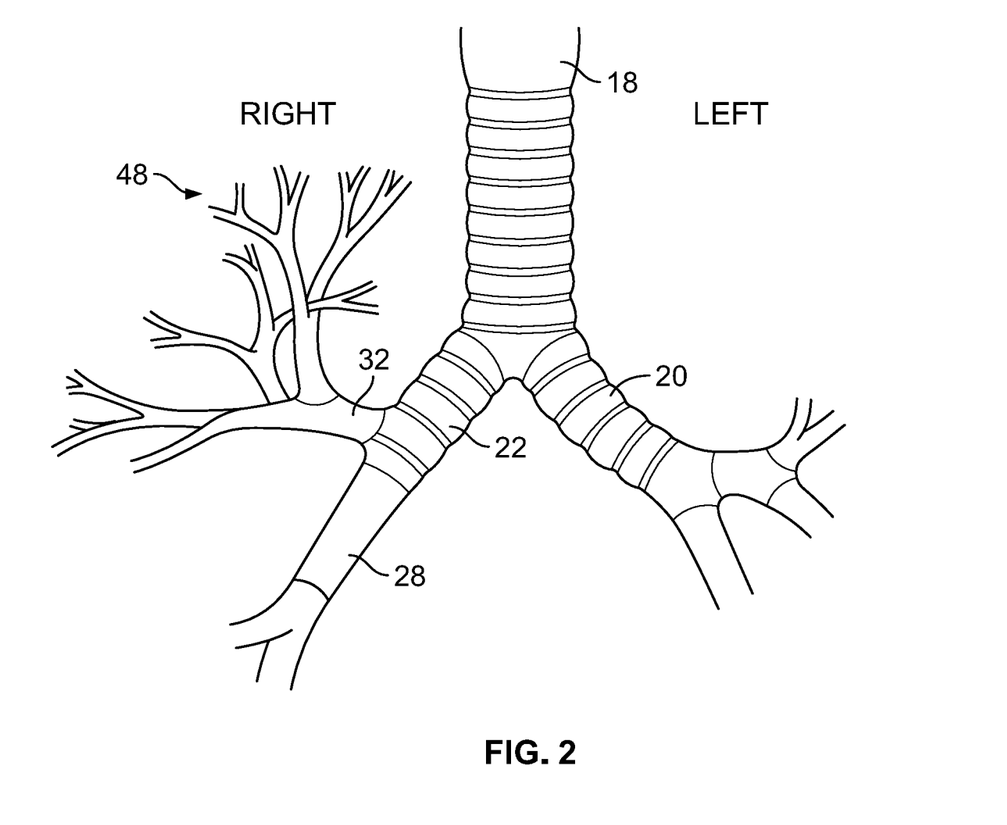
FIG. 2 illustrates the airway in the respiratory system.

FIG. 2 is a perspective view of the airway anatomy emphasizing the upper right lung lobe 48. In addition to the bronchial branches illustrated in FIG. 1, FIG. 2 shows sub-segmental bronchial branches (fourth generation) that provide air circulation (i.e. ventilation) to superior right lung lobe 48. The bronchial segments branch into six generations and the bronchioles branch into approximately another three to eight generations or orders. Each airway generation has a smaller diameter than its predecessor, with the inside diameter of a generation varying depending on the particular bronchial branch, and further varying between individuals. A typical lobar bronchus providing air circulation to the upper right upper lobe 48 has an internal diameter of approximately 1 cm. Typical segmental bronchi have internal diameter of approximately of about 4 to about 7 mm.

The airways of the lungs branch much like the roots of a tree and anatomically constitute an extensive network of air flow conduits that reach all lung areas and tissues. The airways have extensive branching that distally communicates with the parenchyma alveoli where gas exchange occurs. Because of these physiological characteristics of the airways, a medium, such as a vapor, delivered through an airway can be delivered focally or more regionally depending largely on the airway location at which the medium is delivered or dispersed.

While not illustrated, a clear, thin, shiny covering, known as the serous coat or pleura, covers the lungs. The inner, visceral layer of the pleura is attached to the lungs and the outer parietal layer is attached to the chest wall 14. Both layers are held in place by a film of pleural fluid in a manner similar to two glass microscope slides that are wet and stuck together. Essentially, the pleural membrane around each lung forms a continuous sac that encloses the lung and also forms a lining for the thoracic cavity 12. The space between the pleural membranes forming the lining of the thoracic cavity 12 and the pleural membranes enclosing the lungs is referred to as the pleural cavity. If the air tight seal around the lungs created by the pleural members are breached (via a puncture, tear, or is otherwise damaged) air can enter the sac and cause the lungs to collapse.

Bronchoscopy Approach

Figure 3:
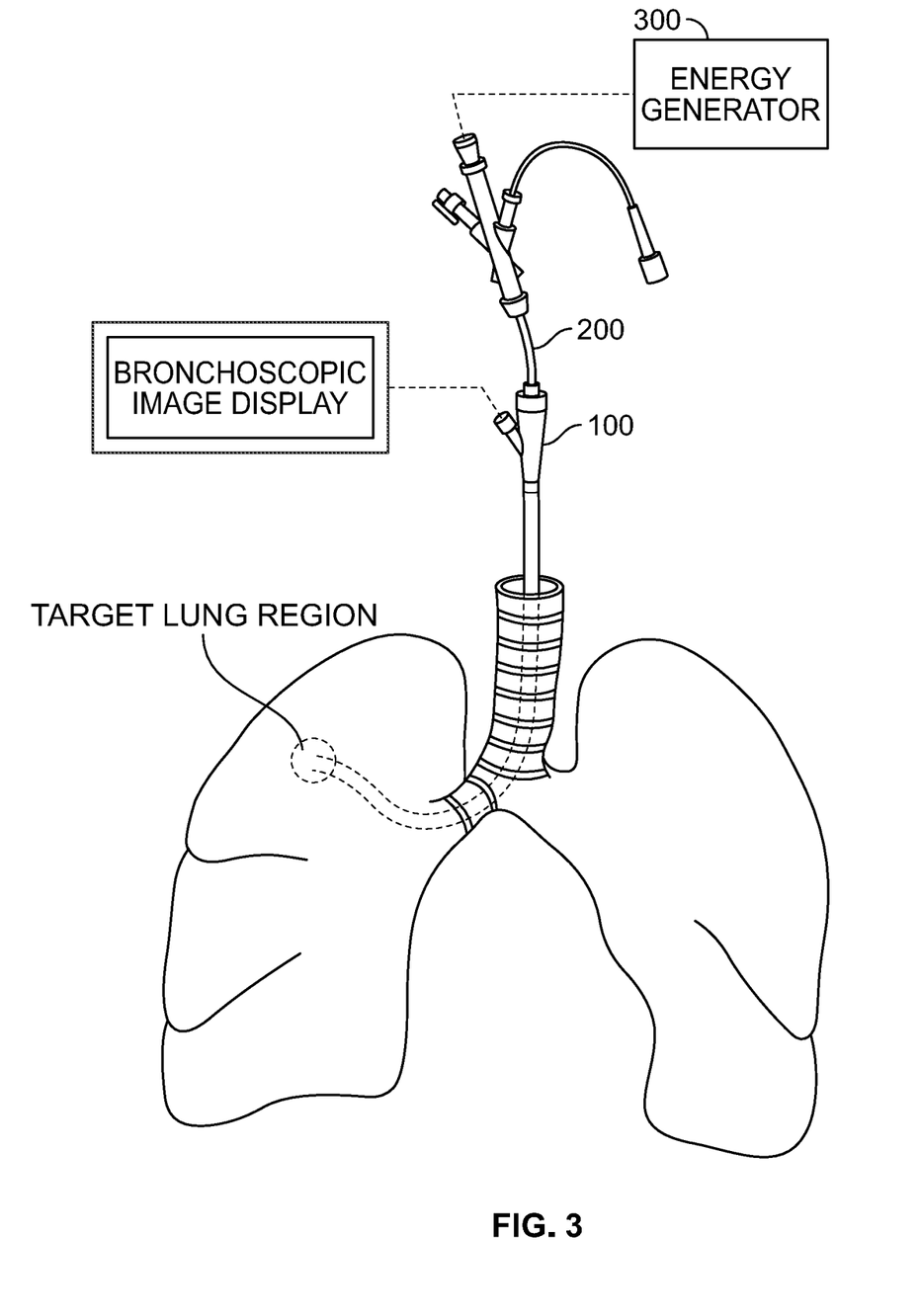
FIG. 3 illustrates one method of treating a volume of lung tissue in accordance with the present invention.

FIG. 3 illustrates a bronchoscopic procedure in accordance with some embodiments of the present invention. FIG. 3 shows a bronchoscope 100 having a working channel into which an energy delivery catheter 200 (or another tool) is inserted. Bronchoscope 100 is inserted into a patient's lungs while the proximal portion of the energy delivery catheter 200 remains outside of the patient. Energy delivery catheter 200 is adapted to operatively couple to an energy generator 300 as further discussed below. Examples of energy delivery catheters include, without limitation, a condensable vapor ablation catheter as described herein.

Energy Generator

Figure 4:
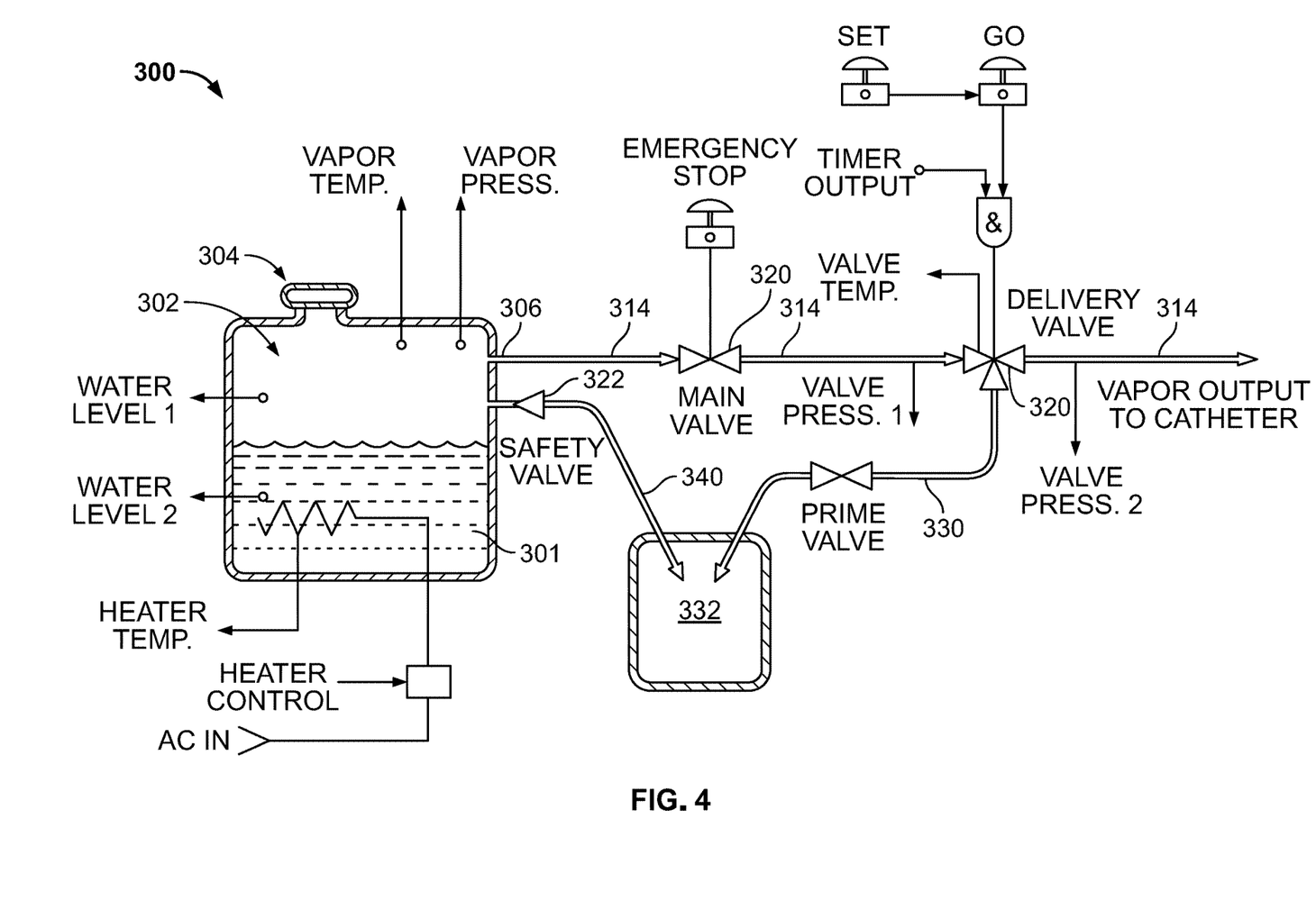
FIG. 4 is a schematic illustrating one embodiment of a vapor generator in accordance with the present invention.

FIG. 4 is a schematic diagram of an energy generator 300 configured as a vapor generator. In embodiments, vapor generator is configured to deliver a controlled dose of vapor to one or more target lung tissues. Vapor generator 300 is adapted to convert a biocompatible liquid 301 (e.g. saline, sterile water or other biocompatible liquid), into a wet or dry vapor, which is then delivered to one or more target tissues. A wet vapor refers to a vapor that contains vaporous forms of the liquid as well as a non-negligible proportion of minute liquid droplets carried over with and held in suspension in the vapor. A dry vapor refers to a vapor that contains little or no liquid droplets. In general, vapor generator 300 is configured to have a liquid capacity between about 1000 to 2500 cc and configured to generate a vapor having a pressure between about 5-100 prig and temperatures between about 100-175° C.

In embodiments, vapor generator 300 is configured as a self-contained, medical-grade generator unit comprising at least a vaporizing unit 302, a vapor inlet 304, and a vapor outlet 306. The vaporizing unit 302 comprises a fluid chamber for containing a fluid 301, preferably a biocompatible, sterile fluid, in a liquid state. In embodiments, vapor outlet 306 is coupled to one or more pipes or tubes 314, which in turn are placed in fluid communication with an energy delivery catheter 200. Vapor flow from vapor generator 300 to a catheter (and specifically a vapor lumen of said catheter) is depicted as a vapor flow circuit 314 wherein flow of the vapor in circuit 314 is indicated by arrows 314 in FIG. 4. In a preferred embodiment, vapor generator is configured to deliver a repeatable dose of vapor to energy delivery catheter 200. The dose of the vapor may vary. Exemplary doses range, without limitation, from 100 to 1000 calories.

Vaporizer unit 302 is configured to heat and vaporize a liquid contained therein. Other components can be incorporated into the biocompatible liquid 301 or mixed into the vapor. For example, these components can be used to control perioperative and/or post procedural pain, enhance tissue fibrosis, and/or control infection. Other constituents, for the purpose of regulating vapor temperatures and thus control extent and speed of tissue heating, can be incorporated; for example, in one implementation, carbon dioxide, helium, other noble gases can be mixed with the vapor to decrease vapor temperatures.

Vaporizing unit 302 is also shown having a fluid inlet 304 to allow liquid 301 to be added to the fluid chamber as needed. Fluid chamber can be configured to accommodate or vaporize sufficient liquid as needed to apply vapor to one or more target tissues. Liquid in vaporizing unit 302 is heated and vaporized and the vapor flows into vapor outlet 306. A number of hollow tubular shafts or pipes 314 are adapted to fluidly connect vapor outlet 306 to the catheter 200.

In embodiments, a flexible hollow tube or umbilical-like cord extends from the generator 300 and terminates in a handle (not shown). The handle is adapted to operatively couple to a variety of types of energy delivery catheters via a hub assembly (such as hub assembly 214 shown in FIG. 5 and discussed herein). In embodiments, the hub assembly or other connecting means is configured to allow for a secure, fluidly sealed, and quick release between the catheter and generator handle. Examples of suitable quick connect and release mechanisms include, without limitation, Luer Lock hub assemblies and fittings.

In embodiments, a catheter and vapor generator are configured to be directly coupled to one another via mating connectors. Vapor delivery is controlled by the generator, a controller external to the generator, or actuating buttons and mechanisms on the catheter itself. For example, the catheter may comprise a handpiece portion to control vapor doses.

Preferably, there is little or no vapor-to-liquid transition during movement of the vapor through vapor flow circuit 314. Vapor flow through vapor flow circuit 314 is unidirectional (in the direction of arrows 314), accordingly one or more isolation valves 320 are incorporated in vapor flow circuit 314. Isolation valves 320, which are normally open during use of generator 300, serve to minimize vapor flow in a direction opposite that of the vapor flow circuit 314.

A priming line 330, branching from main vapor flow circuit 314, is provided to minimize or prevent undesirable liquid-state water formation during vapor flow through vapor flow circuit 314. Pressure and temperature changes along vapor flow circuit 314 can affect whether the vapor is sustainable in a vapor state or condensed back into a liquid. Priming line 330 is provided to equalize temperatures and/or pressures along vapor flow circuit 314 in order to minimize or prevent undesirable liquid-state transition of the vapor during its progression through vapor flow circuit 314. In one embodiment, an initial "purge" or "priming" procedure can be performed prior to delivery of a therapeutic vapor dose in order to preheat flow circuit 314 thus maintaining a constant temperature and pressure in the main vapor flow circuit 314 prior to delivery of a vapor to the target lung tissue.

As shown in FIG. 4, priming line 330 terminates at evaporator 332, which is adapted to either house undesirable liquid in a collection unit (not shown) located within generator 300. In one embodiment, collection unit is adapted to house the liquid until a user or clinician is able to empty said collection unit. Alternatively, evaporator 332 is configured to evaporate and expel said undesirable liquid into the ambient air. Baffle plates (not shown) or other like means can be incorporated in evaporator 332 to facilitate maximal vapor-to-liquid transition. It should be understood that other suitable evaporator configurations could be included to facilitate vapor-to-liquid transition during a priming procedure of lines 314.

A number of sensors, operatively connected to a controller, can be incorporated into vapor generator 300, for example, in the liquid chamber, or along any point in vapor flow circuit 314. Water level sensors, adapted to monitor the water level in the liquid chamber, can be included. These water level sensors are configured as upper and lower security sensors to sense or indicate when a liquid level in the fluid chamber is below or above a set fluid level. For example, if a water level in the fluid chamber falls below the level of a lower water control sensor, the controller can be also configured to interrupt the operation of the vapor generator 300.

In yet another embodiment, pressure sensors, or manometers, can be included in vaporizing unit 302, or at various points along the vapor flow circuit 314, to measure the liquid or vapor pressures at various discrete locations and/or to measure vapor pressures within a defined segment along circuit 314. One or more control valves 320 can also be installed at various points in the vapor flow circuit 314 to control vapor flow, for instance, to control or increase the vapor flow or vapor flow rates in vapor flow circuit 314.

In yet another embodiment, a safety valve 322 can be incorporated into the liquid chamber of vaporizing unit 302 and coupled to a vapor overflow line 340 if the need for removing or venting vaporizing unit 302 arises during generator 300 operation.

Although the vapor generator is described above having various specific features, the components and configurations of the vapor generator and catheter systems may vary. Additional vapor ablation systems are described in, for example, U.S. Patent Publication No. 2015/0094607 to Barry et al., and U.S. Pat. No. 8,585,645 to Barry et al.; U.S. Pat. No. 7,913,698 to Barry et al., and U.S. Pat. No. 8,322,335 to Barry et al., and U.S. Pat. No. 7,993,323 to Barry et al.

In other embodiments, a condensable vapor is created in the handle portion of the catheter system. Consequently, a separate vapor generator unit is not required. Systems including a resistive heater are described in, for example, U.S. Patent Publication No. 2016/0220297 to Kroon et al. and U.S. Patent Publication No. 2014/0276713 to Hoey et al. Indeed, embodiments of the invention include a wide range of mechanisms to create and transport vapor through the working catheter as described herein.

Vapor Ablation Catheter

Figure 5:
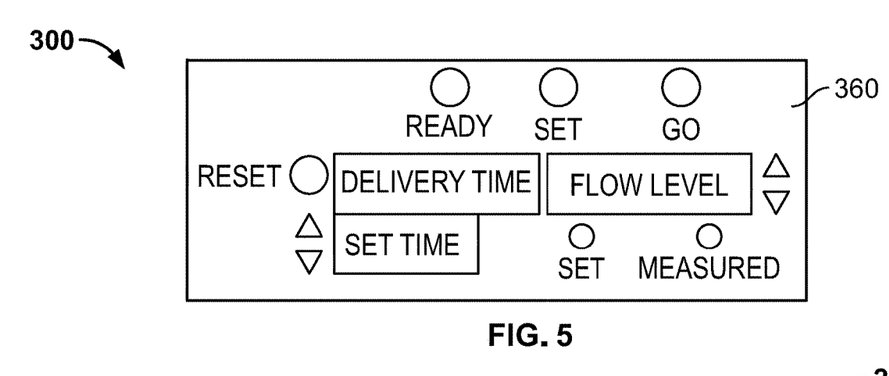
FIG. 5 illustrates one embodiment of a generator display or user interface.

FIG. 5 illustrates one embodiment of a user interface 360 of vapor generator 300. As illustrated, the user interface 360 comprises various visual readouts intended to provide clinical users information about various treatment parameters of interest, such as pressure, temperature and/or duration of vapor delivery. Vapor generator 300 can also be adapted to incorporate one or more auditory alerts, in addition or in lieu of, visual indicators provided on user interface 360. These one or more auditory alerts are designed to provide an alert to a clinical user, such as when vapor delivery is complete, when liquid chamber must be refilled or the like. As will be recognized by those in the art, other components, while not shown, can be incorporated including any of the following: a keyboard; a real-time imaging system display (such as a CT, fluoroscopy, ultrasound); memory system; and/or one or more recording systems.

Figure 6:
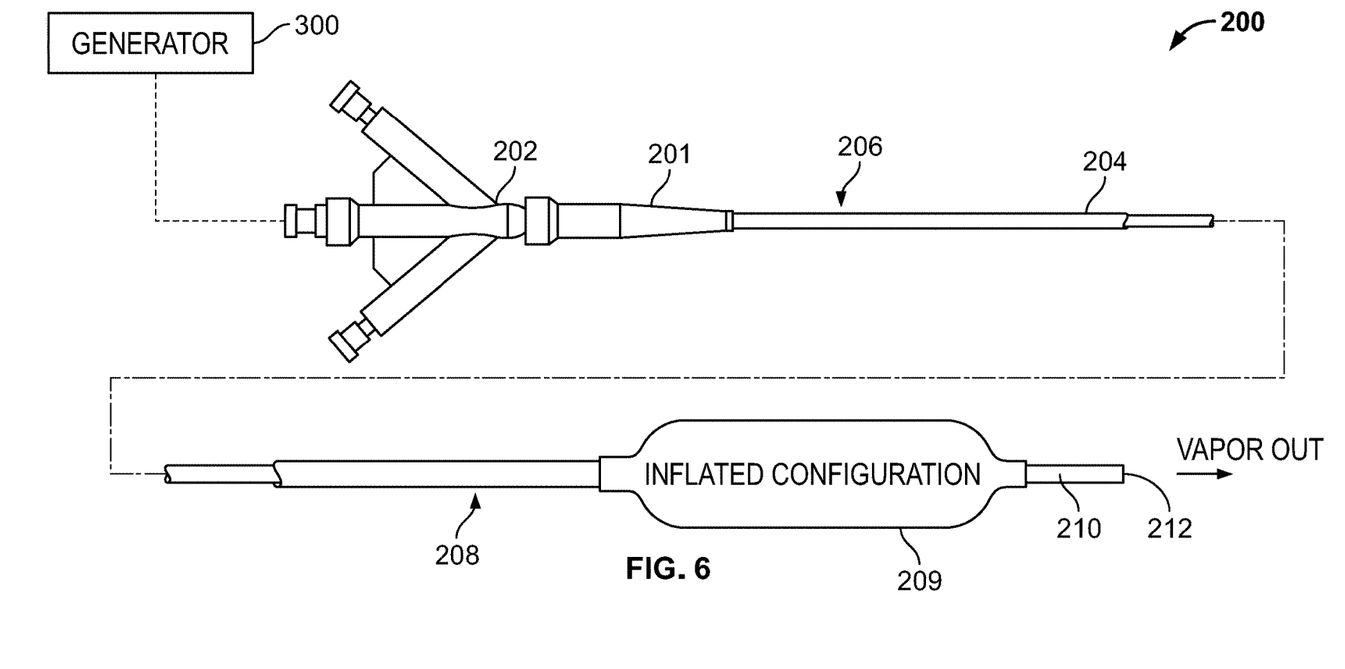
FIG. 6 is a perspective view of one embodiment of an energy delivery catheter in accordance with present invention.

FIG. 6 illustrates yet another aspect of the invention, in particular a vapor catheter 200 embodying various features of the present invention. Generally, catheter 200 is adapted to operatively connect to a control handle of vapor generator 300 via hub assembly 202. Catheter 200 includes elongate shaft 204 defined by proximal section 206 and distal section 208. Elongated shaft 204 is formed with at least one lumen (such as a vapor, inflation, sensing, imaging, guide wire, vacuum lumen) extending from proximal section 206 to distal section 208 of shaft 204. Starting at proximal section 206, catheter 200 comprises strain relief member 201.

Elongated shaft 204 further comprises at least one occlusive member 210 disposed at distal section 208 and distal tip 210 having at least one distal port 212. In one embodiment, the at least one distal port 212 is configured as a vapor outlet port. In yet another embodiment, vapor outlet port may also be used as an aspiration port while catheter is coupled to a vacuum source (not shown) in order to aspirate mucus, fluids, and other debris from an airway through which catheter 200 is advanced prior to vapor delivery. Alternatively, catheter 200 can be configured to include a separate vacuum lumen and aspiration ports as needed. Distal tip 210 can be adapted into a variety of shapes depending on the specific clinical need and application. For example, distal tip 210 can be adapted to be atraumatic in order to minimize airway damage during delivery.

The dimensions of the catheter are determined largely by the size airway lumen through which the catheter must pass in order to deliver the catheter to an airway location appropriate for treatment of the one or more target tissues. An airway location appropriate for treatment of a target lung tissue depends on the volume of the target tissue and the proximity of catheter tip to the target tissue. Generally, catheter 200 is low profile to facilitate placement of catheter distal tip 210 as close as practicable to proximally and peripherally located target lung tissue, i.e. in order to facilitate the catheter's advancement into smaller and deeper airways. In addition, the low profile feature of catheter 200 also ensures that catheter can be delivered to the lungs and airways through a working channel of a bronchoscope, including for example, through the working channels of ultra-thin bronchoscopes. Preferably, catheter 200 is slidably advanced and retracted from a bronchoscope working channel. The overall length and diameter of catheter 200 can be varied and adapted according to: the specific clinical application; size of the airway to be navigated; and/or the location of the one or more target tissues.

Occlusive member or members 210 are similarly configured to provide the smallest possible size when deflated to facilitate ready retraction of catheter 200 back into the working channel of a bronchoscope following completion of a treatment procedure involving delivery of one or more vapor doses to one or more target tissues. The one or more occlusive members 210 are provided to obstruct of proximal vapor flow and/or seat catheter 200 in the patient's airway during vapor delivery without slipping.

Obstruction of an airway by occlusive member 210 prevents retrograde flow of vapor to tissues located outside of the desired target tissues. Because of the physiological characteristics of the airways, in particular the fact that the airways ventilate and communicate specific lung parenchyma or tissues, vapor delivered or dispersed at a particular airway location (e.g. at the bronchial, sub segmental, main bronchi) determines whether there is a focal or regional heating of tissue. In addition to location of the catheter distal tip, other considerations that impact whether there is focal or regional tissue heating patterns (i.e. volume of tissue heated or size of thermal lesion) created include: time or duration of vapor delivery; the vapor flow rate; and vapor content (dry vs. wet; vapor alone vs. vapor cocktail). Preferably, the one or more occlusive members 210 are compliant to ensure: adequate seating; airway obstruction; and/or complete collapse following deflation.

Catheter 200 can be fabricated from a variety of suitable materials and formed by any process such as extrusion, blow molding, or other methods well known in the art. In general, catheter 200 and its various components are fabricated from materials that are relatively flexible (for advancement into tortuous airways) yet having good pushability characteristics and durable enough to withstanding the high temperatures and pressures of the vapor delivered using catheter 200.

Catheter 200 and elongated shaft 204 can be a tubular braided polyimide, silicone, or reinforced silicone. These materials are relatively flexible, yet have good pushability characteristics, while able to withstand the high temperature and pressures of vapor flow. Suitable materials should be adapted to withstand vapor pressures of up to 80 prig, at temperatures up to 170 degrees C. Specific suitable materials include, for example, various braided polyimide tubing available, for example, from IW High Performance Conductors, Inc. Similarly, the one or more occlusive members 210 are preferably fabricated from similar materials having pressure and temperature tolerant attributes as elongated shaft 204, but preferably which is also compliant, such as silicone available from Dow Corning Q74720. As an added feature, catheter 200 and elongated shaft 204 can further be adapted to include varying flexibility and stiffness characteristics along the length of shaft 204 based on the clinical requirements and desired advantages. While not shown, various sensing members, including for example pressure, temperature and flow sensors known in the art can be incorporated into catheter 200. For example, catheter 200 can be adapted to include a sensing lumen for advancement or connection with various sensory devices such as pressure, temperature and flow sensors.

Figure 7:
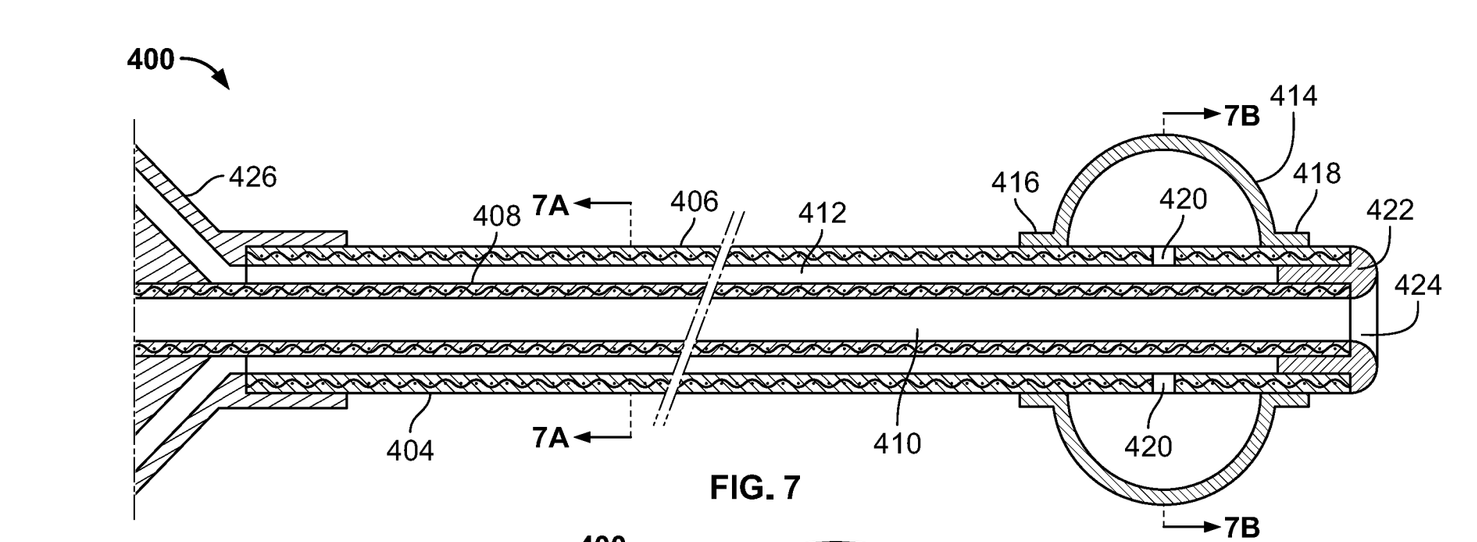
FIG. 7 is a longitudinal cross-sectional view of yet another embodiment of a catheter in accordance with the present invention.
Figure 7A:
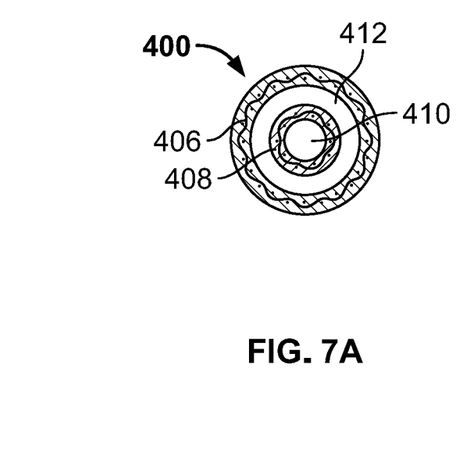
FIG. 7A transverse a cross-sectional view of the catheter of FIG. 7 taken along lines 7A-7A.
Figure 7B:
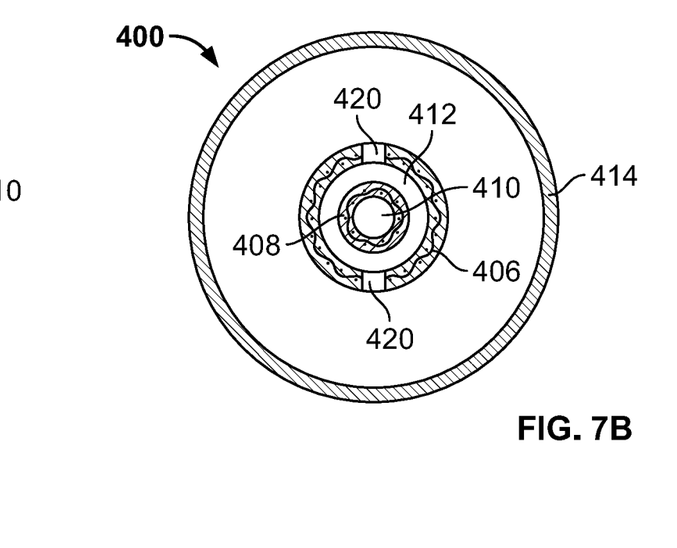
FIG. 7B is a transverse cross-sectional view of catheter illustrated in FIG. 7 taken along lines 7B-7B.

Turing now to FIG. 7, illustrated is a preferred embodiment of a vapor catheter 400. FIG. 7 is a longitudinal cross sectional view of the elongate shaft 404 while FIGS. 7A and 7B show transverse cross sectional views of the elongate shaft 404 taken along the lines 7A-7A and lines 7B-7B respectively.

In this preferred embodiment, catheter 400 comprises an elongated catheter shaft 404 having an outer tubular member 406 and an inner tubular member 408 disposed within outer tubular member 406. Inner tubular member 408 defines a vapor lumen 410 adapted to receive a vapor and which is in fluid communication with a vapor flow circuit 314 of generator 300. The coaxial relationship between outer tubular member 406 and inner tubular member 408 defines annular inflation lumen 412. Vapor lumen 410 terminates at vapor port 424.

Inflation balloon 414 is disposed on a distal section of elongated catheter shaft 404 and having proximal 416 and distal 418 balloon ends sealingly secured to outer tubular member 406. One or more inflation ports 420 are disposed on outer tubular member 406 between the proximal 416 and distal 418 ends of inflation balloon 414 so that the interior of inflation balloon 414 is in fluid communication with inflation lumen 412. (See FIG. 7B.)

As shown in FIG. 7, structural members 422 are disposed between inner tubular member 408 and outer tubular member 406 at distal vapor port 424 to seal inflation lumen 412 and provide structural integrity at the catheter tip. Structural members 422 are preferably made of stainless steel, nickel titanium alloys, gold, gold plated materials or other radiopaque materials, to provide catheter tip visibility under fluoroscopy and/or provide sufficient echogenicity so that the catheter tip is detectable using ultrasonography. Hub assembly 426 (or other adaptor) at the proximal end of catheter 400 is configured to direct an inflation fluid (such as a liquid or air) into inflation lumen 412 as well as provide access to vapor lumen 410.

FIG. 7B illustrates inflation balloon 414 in an inflated or expanded configuration. Inflation balloon 414 inflates to a cylindrical cross section equal to that of a target airway in order to obstruct the airway and prevent proximal or retrograde vapor flow. This inflated configuration is achieved at an inflation pressure within the working pressure range of balloon 414. Inflation balloon 414 has a working length, which is sufficiently long to provide adequate seating in a target airway without slippage during or prior to vapor delivery.

Suitable dimensions for the vapor catheter 400 in accordance with the present invention include an outer tubular member 406 which has an outer diameter of about 0.05 to about 0.16 inches, usually about 0.065 inches and an inner diameter of about 0.04 to about 0.15 inches, usually about 0.059 inches. The wall thickness of outer tubular member 406 and inner tubular member 408 can vary from about 0.001 to about 0.005 inches, typically about 0.003 inches. The inner tubular member 408 typically has an outer diameter of about 0.04 to about 0.15 inches, usually about 0.054 inches and an inner diameter of about 0.03 to about 0.14 inches, usually about 0.048 inches.

The overall working length of catheter 400 may range from about 50 to about 150 cm, typically about 110 to about 120 cm. Preferably, inflation balloon 414 has a total length about 5 to about 20 mm; a working length of about 1 to about 18 mm, preferably about 4 to about 8 mm. Inflation balloon 414 has an inflated working outer diameter of about 4 to about 20 mm, preferably about 4 to about 8 mm within a working pressure range of inflation balloon 414. In preferred embodiment, outer tubular member 406 and inner tubular member 408 is braided polyimide tubular member from IWG High Performance Conductors. Specifically, the braided polyimide tubular member comprises braided stainless steel, with the braid comprising rectangular or round stainless steel wires. Preferably, the braided stainless steel has about 90 picks per inch. The individual stainless steel strands may be coated with heat resistant polyimide and then braided or otherwise formed into a tubular member or the stainless steel wires or strands may be braided or otherwise formed into a tubular product and the braided surfaces of the tubular product may be coated with a heat resistant polyimide.

As will be appreciated by those skilled in the art, the catheters and generators of the present invention can be used to heat one or more target lung tissue to treat a variety of lung diseases and conditions, including but not limited to: lung tumors, solitary pulmonary nodules, lung abscesses, tuberculosis, as well as a variety of other diseases and disorders. In one embodiment, a procedure for inducing lung volume reduction (as a treatment for emphysema) involves advancing catheter 400 into a segmental or sub-segmental airway and delivering a controlled vapor dose. As will be appreciated by those skilled in the art, the vapor carries most of the energy and heat required to convert liquid in vapor generator from a liquid into a vapor. Upon dispersion of the vapor into the airways, the vapor penetrates into the interstitial channels between the cells, and distributes thermal area over a relatively large volume of tissue, permitting tissue heating to be accomplished quickly, usually with a few seconds or minutes. Vapor heating of target lung tissue is intended to cause tissue injury, shrinkage and/or ablation, in order to cause volumetric reduction of one or more target lung tissues. Lung volume reduction is immediate and/or occurs over several weeks or months.

Depending on the extent of the volumetric reduction (complete or partial reduction of a lobe) desired, catheter 400 is navigated into one or more airways, preferably as into the segmental or sub-segmental airways and the vapor delivered into as many airways as need during a single procedure to effect the therapeutically optimal extent of lung volume reduction. In a preferred embodiment, a vapor generator configured to create a vapor having a vapor pressure between about 5-50 prig, at a temperature between about 100-170 degrees Celsius. within vapor generator 300 is employed. The vapor catheter is delivered into the sub-segmental airways that communicate with either the left and right upper lobes, and vapor delivered for a period of 1-20 seconds in each of these airways, to effect volumetric reduction of the left and right upper lobes. Preferably, energy deliver to a target lung tissue is achieved without attendant plural heating sufficient to cause damage to the pleura or a pneumothoraxes.

Vapor Ablation in Combination with LVR

In embodiments, thermal vapor ablation is combined with other lung volume reduction treatment modalities. For example, and with reference to FIG. 8, a modality to reduce the volume of the emphysematous tissue 560 includes creating one or more openings 512 through the airway walls 500 prior to delivering the condensable vapor. The surgically created openings 512 serve to release trapped air from the diseased tissue 560.

Figure 8:
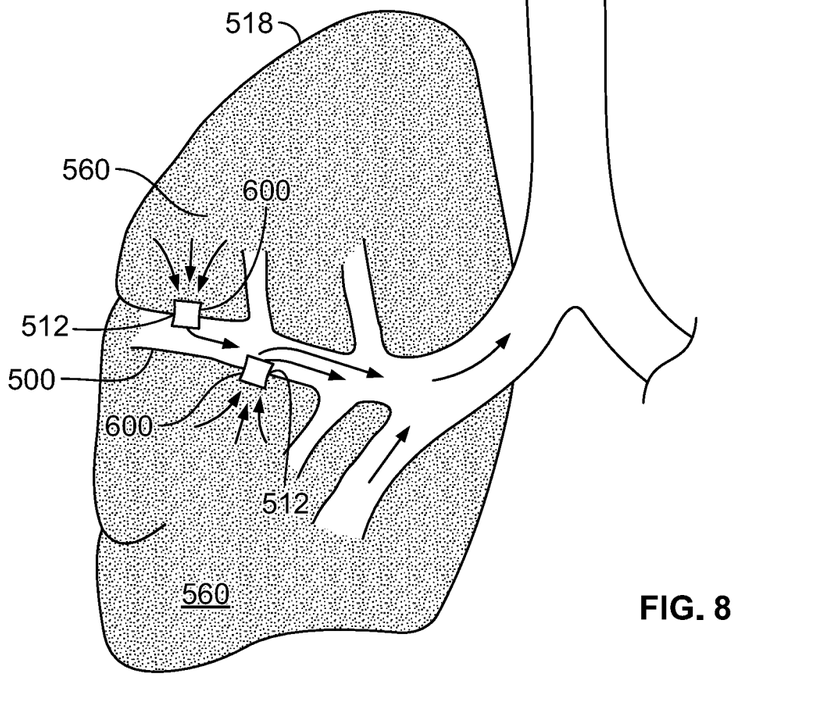
FIG. 8 is an illustration depicting a plurality of collateral channels installed along an airway and serving to release trapped air from the lung.

The openings 512 can optionally be maintained with conduits 600. Without intending to be bound by theory, the treatment of emphysematous tissue is improved by creating alternative airway passageways 512 for the trapped gas to escape from the lung 518. The collateral channels 512 provide new passageways for the air to escape, and reduce the volume of the diseased lung tissue, decrease hyperinflation and residual volume.

Figure 12:
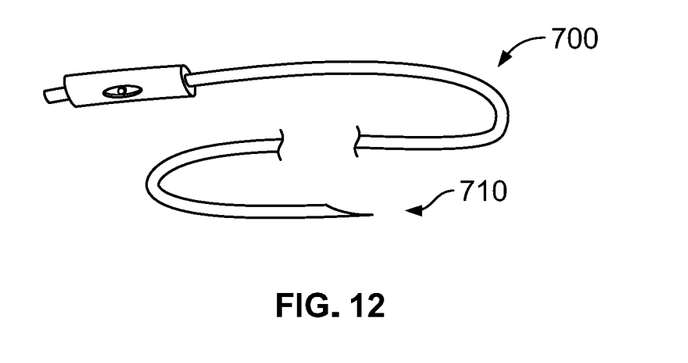
FIGS. 12-14 are illustrations of a piercing member, electrical ablation probe, and dilator, respectively.
Figure 13:
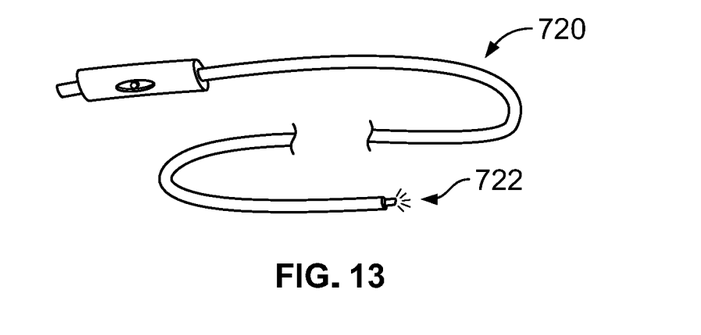

Exemplary catheters for making the openings include elongate flexible catheters comprising a piercing member or electrosurgical probe at the distal end. An example of a piercing member 700 is shown in FIG. 12 and includes a needle-like tip 710. An example of an electrosurgical probe 720 is a monopolar RF ablation probe comprising an active electrode 722 as shown in FIG. 13. A base or return electrode placed on the patient is not shown. Alternately, bi polar or resistive-type ablation tips may be incorporated into the design to form the openings through the airway walls.

Figure 14:
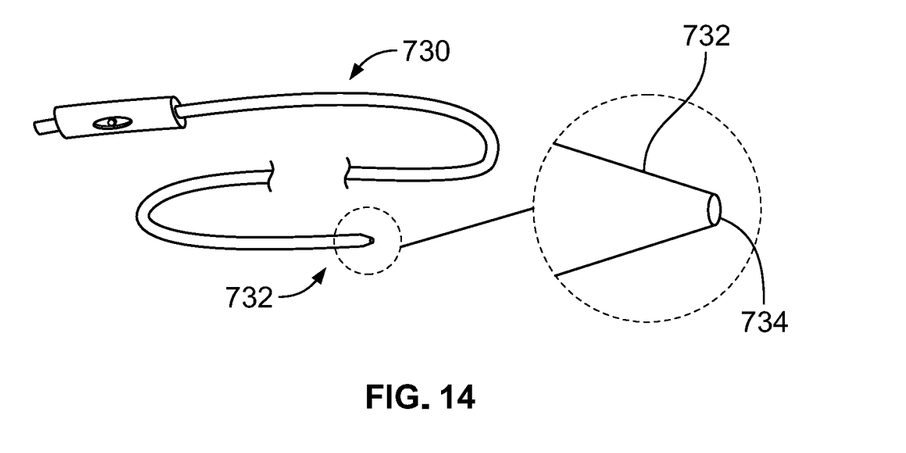

The openings may be enlarged with a dilator. Examples of dilators include inflation or expandable members as well as fixed tapered elongate shafts. An example of a dilator 730 having a taper 732 is shown in FIG. 14. A working lumen 734 may extend through the dilator such that the dilator may be advanced over the piercing member or otherwise guided to the opening.

Exemplary techniques for identifying locations to create the openings, and for creating the openings are described in U.S. Pat. Nos. 6,692,494; 7,393,330; 8,409,167; 9,421,070 and US Patent Publication No. 2004/007315.

A challenge with treating emphysema by creating such openings, however, is to maintain the openings for a clinically significant time after the first procedure. If the openings are not maintained patent, and become occluded, the lungs re-hyperinflate.

As described herein, embodiments of the invention address the above-mentioned challenge by applying thermal vapor ablation to the lung tissue after the collateral channels have been created and in some embodiments, after the lung tissue is a reduced volume state. In a sense, the thermal vapor ablation fixes or seals the lung tissue in the reduced volume state.

Figure 9:
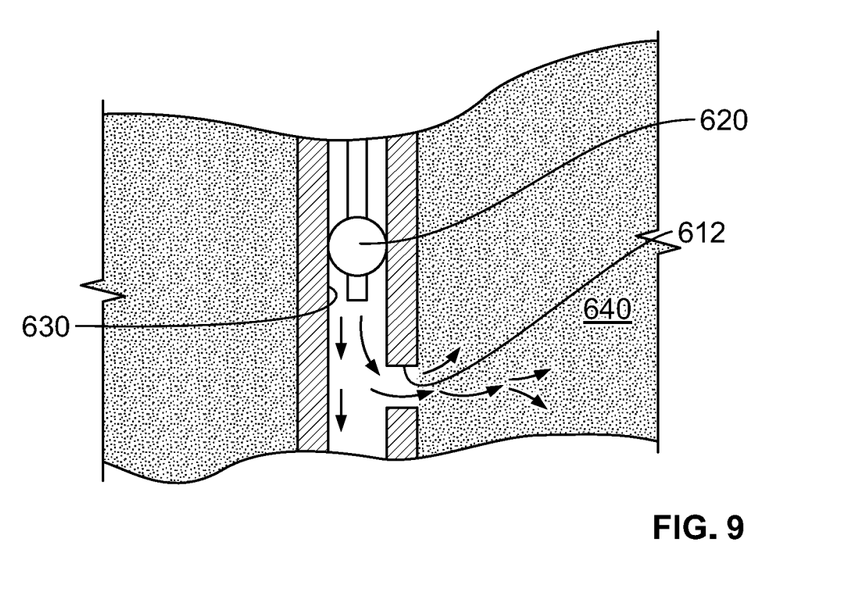
FIG. 9 is an illustration depicting a vapor delivery catheter delivering vapor in an airway in the vicinity of a surgically created channel.

With reference to FIG. 9, a surgically created opening 612 is shown in an airway wall 630. A vapor delivery catheter is shown advanced along the airway lumen 630 to a location in the vicinity of the opening 612. Vapor is shown being delivered from the end of the catheter, and into the lumen 630. The vapor flows along the airway, through the opening 612, and to the diseased tissue 640. Additionally, a balloon 620 is shown deployed within the airway lumen to contain the vapor to the targeted distal areas.

Figure 10:
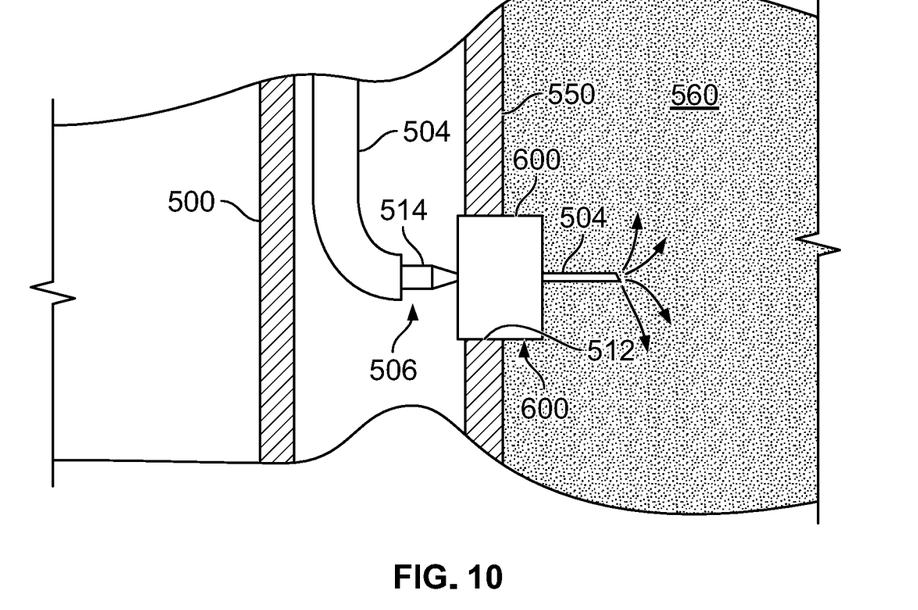
FIG. 10 is an illustration depicting a vapor delivery catheter delivering vapor through a surgically created opening.

In another embodiment, and with reference to FIG. 10, a surgically created opening is shown in the wall. A conduit 600 is deployed in the opening to maintain patency.

A vapor delivery catheter 506 is advanced through the opening 512 and beyond the airway wall. Particularly, the end of the catheter is shown in the parenchymal tissue 560. The catheter is activated at this "shooting" position to disperse the vapor to the diseased tissue, beyond the airway wall and to ablate the hyperinflated parenchymal tissue 560.

Figure 11:
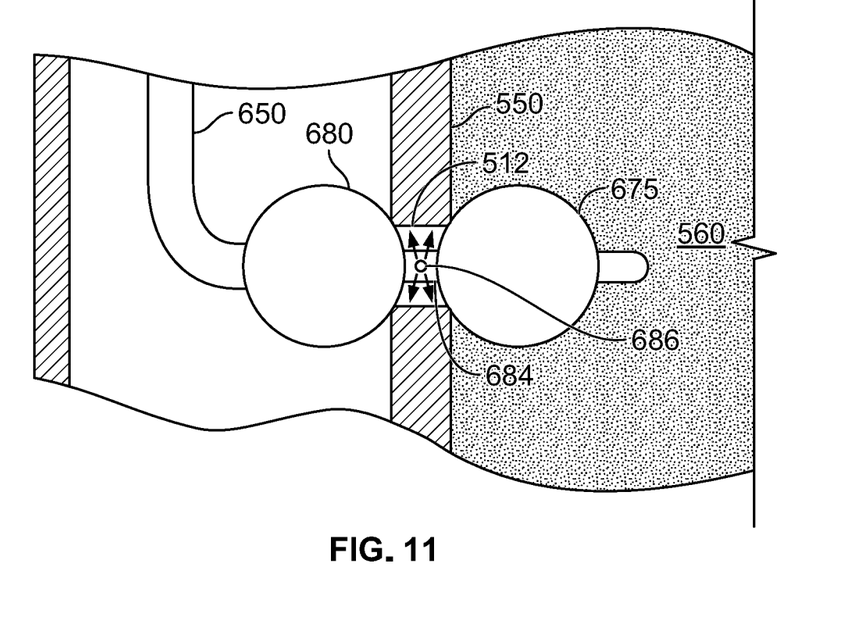
FIG. 11 is an illustration depicting a dual-balloon vapor delivery catheter delivering vapor to only a surgically created opening.

In another embodiment, and with reference to FIG. 11, a surgically created opening 512 is initially created in the airway wall 550. The lung tissue may initially decrease in volume to some degree as trapped air flows through the newly created opening.

Next, catheter 650 advanced into the opening 512. The catheter 650 is shown with a dual balloon 675, 680 type structure. The two balloons are axially separated by a shaft portion 684 comprising an egress aperture 686. The vapor delivery catheter is manipulated through the opening 550 in a deflated state, and both balloons are inflated. The inflated balloons isolate the surgically created opening 512. The ablation catheter is then activated and delivers the vapor from the egress aperture 686 to the opening 512 only. The balloons 675,680 contain the vapor to the opening-only. Without intending to be bound by theory, it is anticipated that applying vapor to the airway opening only serves to seal the opening and prohibit the opening from premature closing.

The above described steps for delivering vapor to the tissue may be combined in any logical manner and the steps may be performed at multiple locations and lung segments within the lung during the same procedure or in additional procedure and after a patient recovery period.

In embodiments, the condensable vapor is delivered first, and then the collateral openings are created through airway walls.

In embodiments, vapor is delivered only distally beyond the opening. In other embodiments, the vapor is delivered only to the airway lumen after the holes have been surgically created. Still in other embodiments, the vapor is delivered and isolated to only to the surgically created openings.

In embodiments, multiple vapor ablations are performed within one procedure. For example, after one or more openings are created through the airway wall, the vapor is delivered into the openings. Then, the vapor delivery catheter is retracted to a new location proximal the opening, and the vapor is delivered to the lumen in fluid communication with the surgically created openings. Indeed, many combinations and variations of the steps and timing are contemplated herein and are intended to all be within the scope of the invention except where such combinations are exclusive to one another.

Catheter Tracking and Guidance

As will be appreciated by one skilled in the art, various imaging techniques (in addition to or in lieu of conventional bronchoscopic imaging) can be employed to assist with the medical interventions described herein. For example, real time fluoroscopy can be used to guide and confirm the position of vapor delivery catheter in the lung. Nonlimiting examples of guidance techniques include video or fluoroscopy based tracking and guidance, and/or electromagnetic based guidance via use of transponders or other sensors or transmitters. A wide variety of systems may be employed to track the location of the distal end of the catheter and other instruments advanced into the lung and to compare or register the location of the devices with previously obtained image data of the patient. Examples of tracking and guidance techniques are described in U.S. Pat. No. 7,233,820 to Gilboa; U.S. Pat. No. 7,756,563 to Higgins et al.; U.S. Pat. No. 7,889,905 to Higgins et al.; U.S. Pat. No. 9,265,468 to Rai et al.; and U.S. Patent Publication No. 20160180529 to Rai et al. See, e.g., the Superdimension™ Navigation System, manufactured by Medtronic (Minneapolis, Minnesota), and the Archimedes™ System, manufactured by Broncus Medical, Inc., (San Jose, California).

Route Planning

Additionally, in embodiments, the physician can preoperatively plan one or more routes through the airways to the target location to perform the procedure described herein. An entire pathway or route may be planned from the mouth or nasal passageway, through the airways, and to the target tissue whether within the lumen or outside of the lumen. Then, the pre-planned or pre-determined route may be used during the procedure to guide the physician. One of the above described guidance techniques can be used to assess the location of the catheter as it is advanced into the target position. Examples of a route planning techniques are described in U.S. Pat. No. 9,037,215 and U.S. Patent Publication No. 2009/0156895, both to Higgins et al. See also the LungPoint® Planner, manufactured by Broncus Medical, Inc., (San Jose, California).

ALTERNATIVE EMBODIMENTS

In embodiments, a staged procedure includes delivering vapor to one or more segments of the lung, and observing whether the segment(s) clinically respond as desired to the vapor treatment. Should the segment not respond as desired, one or more surgically created openings can be formed in the offending lung segment. Then, a method includes delivering a second dose of thermal condensable vapor through the surgically created openings to the diseased lung segments that were unaffected by the initial vapor treatment.

In another embodiment, a method for treating bulla includes creating one or more openings leading to the bulla, and advancing the catheter through the openings. Once the position is confirmed, vapor is delivered to the bulla to achieve the reduction of bulla.

In another embodiment, the method comprises applying vapor through the openings-only for lung volume reduction and to preserve the mucociliary transport system.

The invention has been discussed in terms of certain embodiments. One of skill in the art, however, will recognize that various modifications may be made without departing from the scope of the invention. For example, numerous variations, changes, and substitutions will now occur to those skilled in the art without departing from the invention. Moreover, while certain features may be shown or discussed in relation to a particular embodiment, such individual features may be used on the various other embodiments of the invention.

The invention claimed is:

1. In a bronchoscopic lung volume reduction (BLVR) procedure of diseased tissue in a lung of a patient, a method comprising:
locating candidate locations for creating holes along one or more airways for reducing the risk of pneumonia in a first lung segment;
creating a plurality of holes along the one or more airways; and
draining, without offending the visceral layer of the pleura, mucus from the first lung segment through the created plurality of holes while the diseased tissue remodels during the BLVR procedure, thereby reducing the risk of pneumonia.

2. The method of claim 1 further comprising fixating the diseased tissue in a collapsed configuration by collagen strands.

3. The method of claim 1 further comprising:
advancing a vapor delivery catheter into the first lung segment; and
delivering an initial dose of condensable vapor from the vapor delivery catheter towards the diseased tissue; and
wherein the step of delivering an initial dose of condensable vapor heats the diseased tissue resulting in the development of the collagen strands, causing the diseased tissue to be reduced in volume.

4. The method of claim 3 further comprising delivering a second dose of condensable vapor to a second lung segment.

5. The method of claim 4 further comprising creating at least one opening through the wall of a second airway in the second lung segment.

6. The method of claim 3 further comprising delivering a second dose of vapor to the first airway and the at least one opening.

7. The method of claim 3 wherein the creating is performed prior to the step of delivering.

8. The method of claim 7 wherein the creating and the delivering are performed within a first medical procedure.

9. The method of claim 7 wherein the creating is performed in a first procedure, and the delivering is performed subsequent to the creating step in a second medical procedure.

10. The method of claim 9 wherein the second medical procedure is at least 8 weeks after the first medical procedure.

11. The method of claim 3 wherein the step of delivering is performed with a vapor delivery catheter comprising an inflatable balloon.

12. The method of claim 1 wherein the creating at least one opening is performed with a device selected from the group consisting of a needle and a RF instrument.

13. The method of claim 1 wherein the remodeling is performed by ablation.

14. The method of claim 1, wherein the holes lack implants.

15. The method of claim 14, wherein the BLVR is performed by ablation.

16. The method of claim 15, wherein the ablation is performed using a vapor delivery catheter.

17. A method for reducing the risk of pneumonia while reducing the volume of diseased tissue in a lung of a patient, the method comprising:
identifying a first lung segment leading to the diseased tissue, the lung segment comprising a first airway;
remodeling, without use of implants, the diseased tissue by fixing the diseased tissue in a reduced state; and
draining liquid from the first lung segment during the remodeling by creating, without offending the visceral layer of the pleura, at least one opening through a wall of the first airway to reduce the likelihood of pneumonia through better liquid clearance of the remodeled first lung segment.

18. The method of claim 17 further comprising fixating the diseased tissue in a collapsed configuration by collagen strands.

* * * * *